(12) United States Patent
Stenman et al.

(10) Patent No.: US 10,471,110 B2
(45) Date of Patent: Nov. 12, 2019

(54) BIFIDOBACTERIA FOR TREATING CARDIAC CONDITIONS

(71) Applicant: DUPONT NUTRITION BIOSCIENCES APS, Copenhagen K (DK)

(72) Inventors: Lotta Stenman, Kantvik (FI); Sampo Lahtinen, Lohja (FI); John Konhilas, Tucson, AZ (US)

(73) Assignee: DuPont Nutrition Biosciences ApS (DK)

( * ) Notice: Subject to any disclaimer, the term of this patent is extended or adjusted under 35 U.S.C. 154(b) by 0 days.

(21) Appl. No.: 15/744,211

(22) PCT Filed: Jul. 7, 2016

(86) PCT No.: PCT/EP2016/066184
§ 371 (c)(1),
(2) Date: Jan. 12, 2018

(87) PCT Pub. No.: WO2017/009187
PCT Pub. Date: Jan. 19, 2017

(65) Prior Publication Data
US 2018/0200311 A1 Jul. 19, 2018

Related U.S. Application Data

(60) Provisional application No. 62/193,537, filed on Jul. 16, 2015.

(30) Foreign Application Priority Data

Aug. 12, 2015 (GB) .................................. 1514303.5

(51) Int. Cl.
*A61K 35/745* (2015.01)
*A23L 33/135* (2016.01)
*A61P 9/00* (2006.01)
*A61K 35/74* (2015.01)

(52) U.S. Cl.
CPC .......... *A61K 35/745* (2013.01); *A23L 33/135* (2016.08); *A61K 35/74* (2013.01); *A61P 9/00* (2018.01); *A23V 2002/00* (2013.01); *A23V 2200/326* (2013.01); *A23Y 2300/21* (2013.01)

(58) Field of Classification Search
None
See application file for complete search history.

(56) References Cited

U.S. PATENT DOCUMENTS

2004/0126356 A1* 7/2004 Pang .................... A61K 35/741
424/85.1

2012/0107291 A1* 5/2012 Burcelin .............. A61K 31/155
424/93.45
2014/0126356 A1  5/2014 Lee et al.

FOREIGN PATENT DOCUMENTS

| CN | 101579361 A | 11/2009 |
|----|-------------|---------|
| CN | 104000190 A | 8/2014 |
| EP | 0181170 A2 | 1/1985 |
| EP | 2808024 A1 | 3/2014 |
| JP | 2003334029 A | 11/2003 |

OTHER PUBLICATIONS

Alander et al. (International Dairy J., 11:817-825, 2001).*
Alander, et al., "Effect of galacto-oligosaccharide supplementation on human faecal microflora and on survival and persistence of Bifidobacterium lactis Bb-12 in the gastrointestinal tract", International Dairy Journal, 2001, vol. 11, pp. 817-825.
Stenman et al., "Potential probiotic Bifidobacterium animalis ssp. lactis 420 prevents weight gain and glucose intolerance in diet-induced obese mice", Beneficial Microbes, 2014, vol. 5, No. 4, pp. 437-445.
Sanaie et al., "Effect of a Probiotic Preparation (VSL#3) on Cardiovascular Risk Parameters in Critically-Ill Patients", Journal of Cardiovascular and Thoracic Research, 2013, vol. 5, No. 2, pp. 67-70.
Alhaj et al., "Hypocholesterolaemic effect of Bifidobacterium animals subsp. lactis (Bb12) and trypsin casein iydrolysate", Food Chemistry, 2010, vol. 123, pp. 430-435.
Ejtahed et al., "Effect of probiotic yogurt containing Lactobacillus acidophilus and Bifidobacterium lactis on lipid profile in individuals with type 2 diabetes mellitus", American Dairy Science Association, 2011, vol. 94, pp. 3288-3294.
Tuohy et al., "Conference on 'Dietary strategies for the management of cardiovascular risk'. The way to a man's heart is through his gut microbiota—dietary pro and prebiotics for the management of cardiovascular risk", Proceedings of the Nutrition Society, 2014, vol. 73, pp. 172-185.
International Preliminary Report on Patentability for International Application No. PCT/EP20161/066184, International Filing Date Jul. 7, 2016.
International Search Report for International Application No. PCT/EP2016/066184, International Filing Date Jul. 7, 2016.
Written Opinion of the International Searching Authority, International Application No. PCT/EP2016/066184, International Filing Date Jul. 7, 2016.

* cited by examiner

Primary Examiner — Brian Gangle

(57) ABSTRACT

This invention relates to new uses of Bifidobacteria (particularly, although not exclusively, probiotic Bifidobacteria), and to food products, feed products, dietary supplements and pharmaceutical formulations containing them. The bacteria are suitable for the treatment of myocardial infarction, dilated cardiomyopathy, inflammatory heart disease (including endocarditis, inflammatory cardiomegaly and myocarditis), and congestive heart failure.

28 Claims, 2 Drawing Sheets

BIFIDOBACTERIA FOR TREATING CARDIAC CONDITIONS

CROSS-REFERENCE TO RELATED PATENT APPLICATIONS

This patent claims priority under 35 USC § 371 as a national phase of Int'l Patent Appl. PCT/EP2016/066184 (filed Jul. 7, 2016; and published Jan. 19, 2017 as Int'l Publ. No. WO2017/009187), which, in turn, claims priority to U.S. Provisional Patent Application No. 62/193,537 (filed Jul. 16, 2015) and United Kingdom Patent Application No. 1514303.5 (filed Aug. 12, 2015). The entire text of each of the above-referenced patent applications is incorporated by reference into this patent.

FIELD OF THE INVENTION

This invention relates to new dosages of *Bifidobacteria* (particularly, although not exclusively, probiotic *Bifidobacteria*), and to food products, feed products, dietary supplements and pharmaceutical formulations containing them.

DESCRIPTION OF THE PRIOR ART

Cardiovascular disease (CVD) remains the leading cause of death in industrialized countries (30% of all global deaths; ref. WHO Fact sheet number 317, Cardiovascular diseases) with 45% of these deaths due to coronary heart disease. Acute coronary events (ACEs) such as myocardial infarction (MI) and/or sudden cardiac death often result from atherosclerotic plaque rupture and the last 15-20 years of research has established a mechanistic link between inflammation in every aspect of the atherosclerotic process including plaque development, rupture and subsequent ACE (Shah P K. Inflammation and plaque vulnerability. *Cardiovasc Drugs Ther* 2009; 23: 31-40).

The use of microorganisms in treating cardiovascular conditions is in general known in the art.

WO 2010/145648 describes generally the use of *Bifidobacteria* to treat a number of cardiovascular conditions, including congestive heart failure and myocardial infarction. In particular, WO 2010/145648 specifically describes the administration of *Bifidobacteria* to mice for a period of 4 weeks, and the effects of the bacteria on glucose tolerance, plasma insulin, weight gain and tissue inflammation.

Glück and Gebbers, *Am. J. Clin. Nutr.* 2003, 77, 517-520, describe the administration of a mixture of probiotics, including *Bifidobacteria*, to humans daily for a period of 3 weeks. The ingested probiotics reduced nasal colonization of pathogenic bacteria such as *Staphylococcus aureus* and *Streptococcus pneumoniae*.

It is generally considered by those skilled in the art that probiotics must be administered for a period of at least 3 weeks to enable them to colonise the gut and exert any therapeutic effect.

SUMMARY OF THE INVENTION

In one aspect, the invention comprises use of a bacterium of the genus *Bifidobacterium* or a mixture thereof in the manufacture of a food product, dietary supplement or medicament for treating cardiovascular disease in a mammal, wherein the bacterium is administered for a period of at least 7 days and not exceeding 18 days.

In a further aspect, the invention comprises a bacterium of the genus *Bifidobacterium* or a mixture thereof for use in treating cardiovascular disease in a mammal wherein the bacterium is administered for a period of at least 7 days and not exceeding 18 days.

In a yet further aspect, the invention comprises a method of treating cardiovascular disease in a mammal, comprising administering to a mammal in need thereof a bacterium of the genus *Bifidobacterium* or a mixture thereof, wherein the bacterium is administered for a period of at least 7 days and not exceeding 18 days.

In one aspect, the invention comprises use of a bacterium of the genus *Bifidobacterium* or a mixture thereof in the manufacture of a food product, dietary supplement or medicament for treating myocardial infarction in a mammal, wherein the bacterium is administered for a period of at least 7 days and not exceeding 18 days.

In one aspect, the invention comprises use of a bacterium of the genus *Bifidobacterium* or a mixture thereof in the manufacture of a food product, dietary supplement or medicament for treating congestive heart failure in a mammal, wherein the bacterium is administered for a period of at least 7 days and not exceeding 18 days.

In one aspect, the invention comprises use of a bacterium of the genus *Bifidobacterium* or a mixture thereof in the manufacture of a food product, dietary supplement or medicament for treating dilated cardiomyopathy in a mammal, wherein the bacterium is administered for a period of at least 7 days and not exceeding 18 days.

In one aspect, the invention comprises use of a bacterium of the genus *Bifidobacterium* or a mixture thereof in the manufacture of a food product, dietary supplement or medicament for treating inflammatory heart disease in a mammal, wherein the bacterium is administered for a period of at least 7 days and not exceeding 18 days.

In a further aspect, the invention comprises a bacterium of the genus *Bifidobacterium* or a mixture thereof for use in treating myocardial infarction in a mammal wherein the bacterium is administered for a period of at least 7 days and not exceeding 18 days.

In a further aspect, the invention comprises a bacterium of the genus *Bifidobacterium* or a mixture thereof for use in treating congestive heart failure in a mammal wherein the bacterium is administered for a period of at least 7 days and not exceeding 18 days.

In a further aspect, the invention comprises a bacterium of the genus *Bifidobacterium* or a mixture thereof for use in treating dilated cardiomyopathy in a mammal wherein the bacterium is administered for a period of at least 7 days and not exceeding 18 days.

In a further aspect, the invention comprises a bacterium of the genus *Bifidobacterium* or a mixture thereof for use in treating inflammatory heart disease in a mammal wherein the bacterium is administered for a period of at least 7 days and not exceeding 18 days.

In a yet further aspect, the invention comprises a method of treating myocardial infarction in a mammal, the method comprising administering to a mammal in need of such treatment a bacterium of the genus *Bifidobacterium* or a mixture thereof, wherein the bacterium is administered for a period of at least 7 days and not exceeding 18 days.

In a still further aspect, the invention comprises a method of treating congestive heart failure in a mammal, the method comprising administering to a mammal in need of such treatment a bacterium of the genus *Bifidobacterium* or a mixture thereof, wherein the bacterium is administered for a period of at least 7 days and not exceeding 18 days.

In a still further aspect, the invention comprises a method of treating dilated cardiomyopathy in a mammal, the method comprising administering to a mammal in need of such treatment a bacterium of the genus *Bifidobacterium* or a mixture thereof, wherein the bacterium is administered for a period of at least 7 days and not exceeding 18 days.

In a still further aspect, the invention comprises a method of treating inflammatory heart disease in a mammal, the method comprising administering to a mammal in need of such treatment a bacterium of the genus *Bifidobacterium* or a mixture thereof, wherein the bacterium is administered for a period of at least 7 days and not exceeding 18 days.

DETAILED DESCRIPTION OF THE INVENTION

Bacteria

Figure 1:
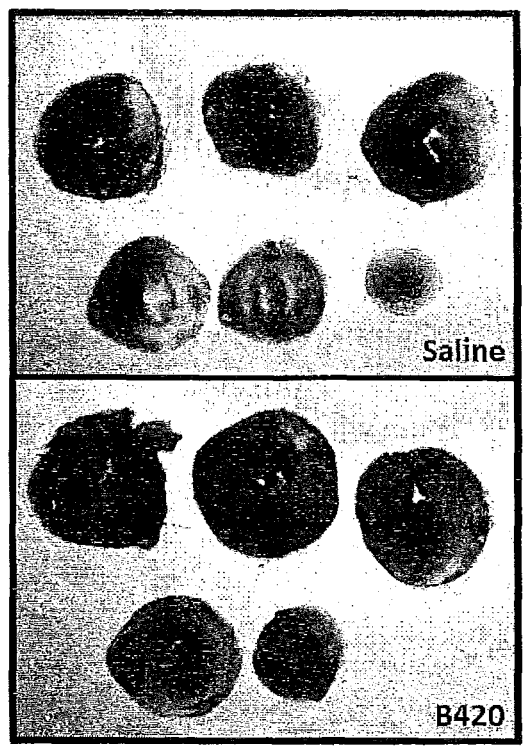
FIG. 1 illustrates the infarct size shown as representative histology in high-fat diet (HFD)-fed mice following a 10-day short term treatment with *Bifidobacterium animalis* subsp. *lactis* strain 420 (B420) according to the present invention (Example 1) and saline (control)

The bacterium used in the present invention is a *Bifidobacterium* or a mixture thereof. Preferably the *Bifidobacterium* to be used in the present invention is a *Bifidobacterium* which is generally recognised as safe and, which is preferably GRAS approved.

The bacterium may be used in any form capable of exerting the effects described herein. For example, the bacteria may be viable, dormant, inactivated or dead bacteria. Preferably, the bacteria are viable bacteria.

The bacteria may comprise whole bacteria or may comprise bacterial components. Examples of such components include bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins.

The bacteria may also or alternatively comprise bacterial metabolites. In this specification the term 'bacterial metabolites' includes all molecules produced or modified by the (probiotic) bacteria as a result of bacterial metabolism during growth, survival, persistence, transit or existence of bacteria during probiotic product manufacture and storage and during gastrointestinal transit in a mammal. Examples include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a sulphurous acid.

Preferably the bacteria comprise whole bacteria, more preferably whole viable bacteria.

Preferably, the *Bifidobacterium* used in accordance with the present invention is one which is suitable for human and/or animal consumption. A skilled person will be readily aware of specific species and or strains of *Bifidobacteria* from within the genera described herein which are used in the food and/or agricultural industries and which are generally considered-suitable for human and/or animal consumption.

In the present invention, the *Bifidobacterium* used may be of the same type (species and strain) or may comprise a mixture of species and/or strains.

Suitable *Bifidobacteria* are selected from the species, *Bifidobacterium bificfium*, *Bifidobacterium longum*, *Bifidobacterium animalis*, *Bifidobacterium breve*, *Bifidobacterium infant's*, *Bifidobacterium catenulatum*, *Bifidobacterium pseudocatenulatum*, *Bifidobacterium adolescentis*, and *Bifidobacterium angulatum*, and combinations of any thereof.

Preferably, the *Bifidobacterium* used in the present invention is of the species *Bifidobacterium animalis*. More preferably, the *Bifidobacterium* used in the present invention is of the species *Bifidobacterium animalis* subsp. *lactis*.

In a particularly preferred embodiment, the bacteria used in the present invention are *Bifidobacterium animalis* subsp. *lactis* strain 420 (B420). This strain is available from DuPont Nutrition Biosciences ApS. This strain of *Bifidobacterium animalis* subsp. *lactis* has also been deposited under the reference DGCC420 by DuPont Nutrition Biosciences ApS, of Langebrogade 1, 1411 Copenhagen K, Denmark, in accordance with the Budapest Treaty on 30 Jun. 2015 at the Leibniz-Institut Deutsche Sammlung von Mikroorganismen und Zeilkulturen GmbH (DSMZ), Inhoffenstrasse 7B, 38124 Braunschweig, Germany, where it is recorded under registration number DSM 32073.

In one embodiment, the bacterium used in the present invention is a probiotic bacterium. In this specification the term 'probiotic bacterium' is defined as covering any non-pathogenic bacterium which, when administered live in adequate amounts, confer a health benefit on the host. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic micro-organisms present in the flora and interactions with the immune system-of the intestine.

In preferred embodiments, the bacterium used in the present invention is a probiotic *Bifidobacterium*.

In some embodiments, the *Bifidobacterium* is used in the present invention together with another probiotic microorganism. Examples of probiotic microorganisms include probiotic bacteria (as defined and exemplified above) and probiotic fungi. Preferably the probiotic microorganisms are probiotic bacteria.

In one embodiment, the additional probiotic bacterium is another bacterium of the genus *Bifidobacterium*, as defined and exemplified above. In another embodiment, the additional probiotic bacterium is a bacterium of a different genus and/or species. Examples of suitable probiotic bacteria include *Akkermansia* ssp. (such as *Akkermansia muciniphila*), *Acetobacter* spp. (such as *Acetobacter xylinum*, *Acetobacter hansenii*, *Acetobacter pasteurianus* and *Aceto-*

*bacter aceti*), *Faecalibacterium* ssp. (such as *Faecalibacterium prausnitzii*), *Leuconostoc* spp., *Bacillus* spp., *Lactobacillus* spp., *Streptococcus thermophilus* or *Pediococcus* sp.

In one embodiment, the additional probiotic bacterium is a bacterium of the genus *Lactobacillus*.

Typically, the *Lactobacillus* bacteria are selected from the species *Lactobacillus acidophilus*, *Lactobacillus casei*, *Lactobacillus kefiri*, *Lactobacillus bifidus*, *Lactobacillus brevis*, *Lactobacillus helveticus*, *Lactobacillus paracasei*, *Lactobacillus rhamnosus*, *Lactobacillus salivarius*, *Lactobacillus curvatus*, *Lactobacillus bulgaricus*, *Lactobacillus sakei*, *Lactobacillus reuteri*, *Lactobacillus fermentum*, *Lactobacillus farciminis*, *Lactobacillus lactis*, *Lactobacillus delbreuckil*, *Lactobacillus plantarum*, *Lactobacillus paraplantarum*, *Lactobacillus crispatus*, *Lactobacillus gassed*, *Lactobacillus johnsonii* and *Lactobacillus jensenii*, and combinations of any thereof.

In preferred embodiments, the *Lactobacillus* bacterium used in the present invention is a probiotic *Lactobacillus*.

Preferably, the *Lactobacillus* bacterium used in the present invention of the species *Lactobacillus acidophilus*.

In one embodiment, the *Bifidobacterium* is used in the present invention together with a bacterium of the species *Lactobacillus acidophilus* strain NCFM. *Lactobacillus acidophilus* NCFM was deposited by Rhodia Chimie, France, at the American Type Culture Collection as PTA-4797 on 15 Nov. 2002.

Dosage

The *Bifidobacterium* (such as a strain of *Bifidobacterium animalis* subsp. *lactis*, for example *Bifidobacterium animalis* subsp. *lactis* strain 420 (B420) are dosed in accordance with the present invention for a period of at least 7 days and not exceeding 18 days.

It has surprisingly been found by the present inventors that, when dosed for the above period, the *Bifidobacterium* exerts unexpectedly favourable cardiac effects. In particular, it has been shown that mammals treated with *Bifidobacterium* for the above period exhibit improvement in various parameters relating to cardiac function compared with mammals which have not been treated with *Bifidobacterium*. This confers the potential for administration of *Bifidobacterium* to prevent, or reduce the probability of suffering from, and/or reduce the impact of, and/or the consequences of, cardiovascular disorders, in particular myocardial infarction, dilated cardiomyopathy, inflammatory heart disease (including endocarditis, inflammatory cardiomegaly and myocarditis) and congestive heart failure.

The improved effect of treatment with *Bifidobacterium* for the above dosing period runs contrary to the teaching of the prior art. It is generally considered by those skilled in the art that probiotics need to be dosed for at least 3 weeks before they can colonise the gut and exhibit any therapeutic effect. It would not therefore have been expected that the *Bifidobacterium* could exhibit any therapeutic effect when dosed for a much shorter period.

The *Bifidobacterium* (such as a strain of *Bifidobacterium animalis* subsp. *lactis*, for example *Bifidobacterium animalis* subsp. *lactis* strain 420 (B420) are dosed in accordance with the present invention for a minimum period of at least 7 days, such as at least 8 days, such as at least 9 days, such as at least 10 days, such as at least 11 days, such as at least 12 days, such as at least 13 days, such as at least 14 days.

The *Bifidobacterium* (such as a strain of *Bifidobacterium animalis* subsp. *lactis*, for example *Bifidobacterium animalis* subsp. *lactis* strain 420 (B420), are dosed in accordance with the present invention for a maximum period of 18 days, such as 17 days, such as 16 days, such as 15 days, such as 14 days, such as 13 days, such as 12 days, such as 11 days.

In one embodiment, the *Bifidobacterium* (such as a strain of *Bifidobacterium animalis* subsp. *lactis*, for example *Bifidobacterium animalis* subsp. *lactis* strain 420 (B420), are dosed in accordance with the present invention for a period of at least 9 days and not exceeding 14 days.

In one embodiment, the *Bifidobacterium* (such as a strain of *Bifidobacterium animalis* subsp. *lactis*, for example *Bifidobacterium animalis* subsp. *lactis* strain 420 (B420) are dosed in accordance with the present invention for a period of at least 10 days and not exceeding 12 days.

The frequency of dosing of the *Bifidobacterium* (such as a strain of *Bifidobacterium animalis* subsp. *lactis*, for example *Bifidobacterium animalis* subsp. *lactis* strain 420 (B420) varies depending on the subject to be treated. Typically, the *Bifidobacterium* (such as a strain of *Bifidobacterium animalis* subsp. *lactis*, for example *Bifidobacterium animalis* subsp. *lactis* strain 420 (B420) are dosed in accordance with the present invention once, twice, three or four times per day for the specified period. Preferably, the *Bifidobacterium* (such as a strain of *Bifidobacterium animalis* subsp. *lactis*, for example *Bifidobacterium animalis* subsp. *lactis* strain 420 (B420) are dosed in accordance with the present invention once per day for the specified period.

The *Bifidobacterium* (such as a strain of *Bifidobacterium animalis* subsp. *lactis*, for example *Bifidobacterium animal's* subsp. *lactis* strain 420 (B420), bacteria used in accordance with the present invention may be administered at a dosage of from about $10^6$ to about $10^{12}$ CFU of bacteria/dose, preferably about $10^7$ to about $10^{11}$ CFU of bacteria/dose. By the term "per dose" it is meant that this amount of bacteria is provided to a subject either per day or per intake, preferably per day. For example, if the bacteria are to be administered in a food product (for example in a yoghurt)—then the food product, e.g. yoghurt will preferably contain from about $10^6$ to $10^{12}$ CFU, more preferably about $10^7$ to about $10^{11}$ CFU, and most preferably about $10^9$ to about $10^{10}$ CFU of the bacteria. If the bacteria are to be administered in a dietary supplement, then the dietary supplement will preferably contain about $10^8$ to about $10^{12}$ CFU, more preferably about $10^9$ to $10^{11}$ CFU of the bacteria. If the bacteria are to be administered in a pharmaceutical composition, then the pharmaceutical composition will preferably contain about $10^8$ to about $10^{12}$ CFU, more preferably about $10^9$ to $10^{11}$ CFU of the bacteria. Alternatively, however, this amount of bacteria may be split into multiple administrations each consisting of a smaller amount of microbial loading so long as the overall amount of bacteria received by the subject in any specific time (for instance each 24 hour period) is within the ranges specified above.

The concentration of the bacteria per g of support varies depending on the intended dose and the nature of the support. In one embodiment, the *Bifidobacterium* (such as a strain of *Bifidobacterium animalis* subsp. *lactis*, for example *Bifidobacterium animalis* subsp. *lactis* strain 420 (B420), bacteria used in accordance with the present invention may be present in a concentration of from 5000 to $10^{13}$ CFU of bacteria/g of support, preferably about $5 \times 10^6$ to about $10^{12}$ CFU of bacteria/g of support. When the support is a food product, such as a yogurt, the bacteria are preferably present in a concentration of from about 5000 to about $5 \times 10^8$ CFU of bacteria/g of food product, preferably about $5 \times 10^6$ to about $5 \times 10^7$ CFU of bacteria/g of food product. When the support is a dietary supplement, the bacteria are preferably present in a concentration of from $10^9$ to about $10^{13}$ CFU/g of dietary supplement, more preferably about $10^{10}$ to $10^{12}$ CFU/g of dietary supplement. When the support is a pharmaceutical composition, the bacteria are preferably present in a concentration of from $10^9$ to about $10^{13}$ CFU/g of dietary supplement, more preferably about $10^{10}$ to $10^{12}$ CFU/g of pharmaceutical composition.

In one embodiment, preferably the *Bifidobacterium* (such as a strain of *Bifidobacterium animalis* subsp. *lactis*, for example *Bifidobacterium animalis* subsp. *lactis* strain 420 (B420), may be administered once per day at a dosage of from about $10^6$ to about $10^{12}$ CFU of bacteria/day, preferably about $10^8$ to about $10^{12}$ CFU of bacteria/day. Hence, the effective amount in this embodiment may be from about $10^6$ to about $10^{12}$ CFU of bacteria/day, preferably about $10^7$ to about $10^{11}$ CFU of bacteria/day. For example, if the bacteria are to be administered in a food product (for example in a yoghurt)—then the bacteria will preferably be administered once per day in a dosage of about $10^6$ to $10^{12}$ CFU of bacteria/day, more preferdbly about $10^7$ to about $10^{11}$ CFU of bacteria/day and most preferably about $10^9$ to about $10^{10}$ CFU of the bacteria/day. If the bacteria are to be administered in a dietary supplement, then the bacteria will preferably be administered once per day in a dosage of about $10^8$ to about $10^{12}$ CFU of bacteria/day, more preferably about $10^9$ to $10^{11}$ CFU of the bacteria/day. If the bacteria are to be administered in a pharmaceutical composition, then the bacteria will preferably be administered once per day in a dosage of about $10^8$ to about $10^{12}$ CFU bacteria/day, more preferably about $10^9$ to $10^{11}$ CFU of the bacteria/day.

CFU stands for "colony-forming units". By 'support' is meant the food product, dietary supplement or the pharmaceutically acceptable support.

When one or more other microorganisms (such as bacteria, preferably probiotic bacteria) are used in combination with the *Bifidobacterium* (such as a strain of *Bifidobacterium animalis* subsp. *lactis*, for example *Bifidobacterium animalis* subsp. *lactis* strain 420 (B420) bacteria in accordance with the present invention), the other bacteria may similarly be administered at a dosage of from about $10^6$ to about $10^{12}$ CFU of microorganism/dose, preferably about $10^7$ to about $10^{11}$ CFU of microorganism/dose. Depending on the manner in which the microorganisms are administered (food product, dietary supplement, or pharmaceutical composition), the preferred amounts of the one or more other microorganisms will typically be in the ranges specified above for *Bifidobacteria*.

Subjects/Medical Indications

The *Bifidobacteria* (and any additional probiotic microorganisms, if present) to which the present invention relates are administered to a mammal, including for example livestock (including cattle, horses, pigs, chickens and sheep), and humans. In some aspects of the present invention the mammal is a companion animal (including pets), such as a dog or a cat for instance. In some aspects of the present invention, the subject may suitably be a human.

The *Bifidobacteria* (and any additional probiotic microorganisms, if present) to which the present invention relates may be suitable for treating a number of diseases or conditions in mammals (particularly humans). In this specification the term "treatment" or "treating" refers to any administration of the *Bifidobacteria* (and any additional probiotic microorganisms, if present) according to the present invention and includes: (1) preventing the specified disease from occurring in a mammal which may be predisposed to the disease but does not yet experience or display the pathology or symptomatology of the disease (including prevention of one or more risk factors associated with the disease); (2) inhibiting the disease in a mammal that is experiencing or displaying the pathology or symptomatology of the diseased (i.e., arresting further development of the pathology and/or symptomatology), or (3) ameliorating the disease in a mammal that is experiencing or displaying the pathology or symptomatology of the diseased (i.e., reversing the pathology and/or symptomatology).

In particular, the use of *Bifidobacteria* according to the present invention is suitable for the treatment of mammals ingesting a high-fat diet. This aspect is discussed in more detail below.

Examples of cardiovascular diseases treatable by use of the *Bifidobacteria* (and any additional probiotic microorganisms, if present) according to the present invention include aneurysm, angina, atherosclerosis, cerebrovascular accident (stroke), cerebrovascular disease, congestive heart failure (CHF), dilated cardiomyopathy, inflammatory heart disease (including endocarditis, inflammatory cardiomegaly and myocarditis), coronary artery disease, myocardial infarction (heart attack) and peripheral vascular disease.

An aneurysm is a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart, a so-called aortic aneurysm). As the size of an aneurysm increases, there is an increased risk of rupture, which can result in severe hemorrhage or other complications including sudden death.

Angina pectoris, commonly known as angina, is severe chest pain due to ischemia (a lack of blood and hence oxygen supply) of the heart muscle, generally due to obstruction or spasm of the coronary arteries (the heart's blood vessels). Coronary artery disease, the main cause of angina, is due to atherosclerosis of the cardiac arteries.

Atherosclerosis is the condition in which an artery wall thickens as the result of a build up of fatty materials such as cholesterol. It is a syndrome affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

A stroke is the rapidly developing loss of brain function(s) due to disturbance in the blood supply to the brain. This can be due to ischemia (lack of blood supply) caused by thrombosis or embolism or due to a hemorrhage. As a result, the affected area of the brain is unable to function, leading to inability to move one or more limbs on one side of the body, inability to understand or formulate speech, or see one side of the visual field and ultimately to death.

Cerebrovascular disease is a group of brain dysfunctions related to disease of blood vessels supplying the brain. Hypertension is the most important cause that damages the blood vessel lining endothelium exposing the underlying collagen where platelets aggregate to initiate a repairing process which is not always complete and perfect. Sustained hypertension permanently changes the architecture of the blood vessels making them narrow, stiff, deformed and uneven which are more vulnerable to fluctuations of blood pressure. A fall in blood pressure during sleep can lead to marked reduction in blood flow in the narrowed blood vessels causing ischemic stroke in the morning whereas a sudden rise in blood pressure can cause tearing of the blood vessels causing intracranial hemorrhage during excitation at daytime. Primarily people who are elderly, diabetic, smoker, or have ischemic heart disease, have cerebrovascular disease. All diseases related to artery dysfunction can be classified under a disease as known as macrovascular disease. This is a simplistic study by which arteries are blocked by fatty deposits or by a blood clot. The results of cerebrovascular disease can include a stroke, or even sometimes a hemorrhagic stroke. Ischemia or other blood vessel dysfunctions can affect one during a cerebrovascular accident.

Heart failure is a global term for the physiological state in which cardiac output is insufficient for the body's needs. This may occur when the cardiac output is low (often termed "congestive heart failure"). Common causes of heart failure include myocardial infarction and other forms of ischemic heart disease, hypertension, valvular heart disease and cardiomyopathy.

Dilated cardiomyopathy is a condition in which the heart becomes enlarged and cannot pump blood efficiently. Dilated cardiomyopathy is the most common form of non-ischemic cardiomyopathy. About one in three cases of congestive heart failure (CHF) is due to dilated cardiomyopathy.

Coronary disease (or coronary heart disease) refers to the failure of coronary circulation to supply adequate circulation to cardiac muscle and surrounding tissue. It is most commonly equated with atherosclerotic coronary artery disease, but coronary disease can be due to other causes, such as coronary vasospasm. It is possible for the stenosis to be caused by the spasm.

Myocardial infarction, commonly known as a heart attack, occurs when the blood supply to part of the heart is interrupted causing some heart cells to die. This is most commonly due to occlusion (blockage) of a coronary artery following the rupture of a vulnerable atherosclerotic plaque, which is an unstable collection of lipids (like cholesterol) and white blood cells (especially macrophages) in the wall of an artery. The resulting ischemia (restriction in blood supply) and oxygen shortage, if left untreated for a sufficient period of time, can cause damage and/or death (infarction) of heart muscle tissue (myocardium).

The *Bifidobacteria* (and any additional probiotic microorganisms, if present) to which the present invention relates are suitable for treating myocardial infarction in a mammal. In one embodiment the term "treating myocardial infarction" comprises preventing, or reducing the probability of suffering from, myocardial infarction. In one embodiment the term "treating myocardial infarction" comprises reducing the impact of, or the consequences of, myocardial infarction. In one embodiment the term "treating myocardial infarction" comprises reducing the size of the myocardial infarction. In one embodiment the term "treating myocardial infarction" comprises increasing or maintaining the ejection fraction subsequent to a myocardial infarction. In one embodiment the term "treating myocardial infarction" comprises decreasing or maintaining the left ventricular volume during systole subsequent to a myocardial infarction. In one embodiment the term "treating myocardial infarction" comprises increasing or maintaining the left ventricular posterior wait dimension during systole subsequent to a myocardial infarction. In each of the above embodiments the reduction, decrease or increase is at least 10%, at least 20%, at least 30%, at least 40%, at least 50%, at least 60%, at least 70%, at least 80%, at least 90% in comparison with a mammal that has not been treated with *Bifidobacteria* (and any additional probiotic microorganisms, if present) according to the present invention.

Peripheral vascular disease (PVD), also known as peripheral artery disease (PAD) or peripheral artery occlusive disease (PAOD), includes all diseases caused by the obstruction of large arteries in the arms and legs, PVD can result from atherosclerosis, inflammatory processes leading to stenosis, an embolism or thrombus formation. It causes either acute or chronic ischemia (lack of blood supply), typically of the legs.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

Diet

As noted above, diabetic and/or obese mammals treated with bacteria according to the present invention may ingest a high-fat diet while mitigating the metabolic consequences of their condition(s). In this specification the term 'high-fat diet' means a diet generally containing at least 20%, preferably at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80%, for example at least 85%, such as at least 90% of calories from fat.

Compositions

While it is possible to administer *Bifidobacteria* (and any additional probiotic microorganisms, if present) alone according to the present invention (i.e. without any support, diluent or excipient), the *Bifidobacteria* (and any additional probiotic microorganisms, if present) are typically and preferably administered on or in a support as part of a product, in particular as a component of a food product, a dietary supplement or a pharmaceutical formulation. These products typically contain additional components well known to those skilled in the art.

Any product which can benefit from the composition may be used in the present invention. These include but are not limited to foods, particularly fruit conserves and dairy foods and dairy food-derived products, and pharmaceutical products. The *Bifidobacteria* (and any additional probiotic microorganisms, if present) may be referred to herein as "the composition of the present invention" or "the composition".

Food

In one embodiment, the *Bifidobacteria* (and any additional probiotic microorganisms, if present) are employed according to the invention in a food product such as a food supplement, a drink or a powder based on milk. Here, the term "food" is used in a broad sense and covers food for humans as well as food for animals (i.e. a feed). In a preferred aspect, the food is for human consumption.

The food may be in the form of a solution or as a solid—depending on the use and/or the mode of application and/or the mode of administration.

When used as, or in the preparation of, a food, such as functional food, the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice, energy drinks, sports drinks and sports nutritional supplements or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods (including snack bars), balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified and non-fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

Still more preferably the food product employed according to the invention is a fermented milk or humanized milk.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a microorganism.

Preferably, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{11}$ cfu. The microorganism according to the present invention may be used before or after fermentation of the yoghurt.

For some aspects the microorganisms according to the present invention are used as, or in the preparation of, animal feeds, such as livestock feeds, in particular poultry (such as chicken) feed, or pet food.

Advantageously, where the product is a food product, the *Bifidobacteria* (and any additional probiotic microorganisms, if present) should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

Food Ingredient

The composition of the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The composition of the present invention may be or may be added to—food supplements (also referred to herein as dietary supplements).

Functional Foods

The composition of the present invention may be or may be added to—functional foods.

As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means, a food which is capable of providing not only a nutritional effect and/or a taste satisfaction, but is also capable of delivering a therapeutic (or other beneficial)

effect to the consumer. Nutraceuticals cross the traditional dividing lines between foods and medicine.

Medicament

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Pharmaceutical

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

A pharmaceutically acceptable support may be for example a support in the form of compressed tablets, tablets, capsules, ointments, suppositories or drinkable solutions. Other suitable forms are provided below.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid depending on the use and/or the mode of application and/or the mode of administration.

The *Bifidobacteria* (and any additional probiotic microorganisms if present) of the present invention may be used as pharmaceutical ingredients. Here, the composition may be the sole active component or it may be at least one of a number (i.e. 2 or more) of active components.

The pharmaceutical ingredient may be in the form of a solution or as a solid—depending on the use and/or the mode of application and/or the mode of administration.

The *Bifidobacteria* (and any additional probiotic microorganisms, if present) may be used according to the present invention in any suitable form—whether when alone or when present in a combination with other components or ingredients. The lactic acid bacteria used in the present invention may be referred to herein as "the composition". Likewise, combinations comprising the composition of the present invention and other components and/or ingredients (i.e. ingredients—such as food ingredients, functional food ingredients or pharmaceutical ingredients) may be used in any suitable form.

The *Bifidobacteria* (and any additional probiotic microorganisms, if present) may be used according to the present invention in the form of solid or liquid preparations or alternatives thereof. Examples of solid preparations include, but are not limited to tablets, capsules, dusts, granules and powders which may be wettable, spray-dried or freeze-dried.

Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

Further examples of form include creams. For some aspects the microorganism used in the present invention may be used in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

Combinations

The composition of the present invention may additionally contain one or more prebiotics. Prebiotics are a category of functional food, defined as non-digestible food ingredients that beneficially affect the host by selectively stimulating the growth and/or activity of one or a limited number of bacteria (particularly, although not exclusively, probiotics, such as *Bifidobacteria* and/or *Lactobacillus*) in the colon, and thus improve host health. Typically, prebiotics are carbohydrates (such as oligosaccharides), but the definition does not preclude non-carbohydrates. The most prevalent forms of prebiotics are nutritionally classed as soluble fibre. To some extent, many forms of dietary fibre exhibit some level of prebiotic effect.

In one embodiment, a prebiotic is a selectively fermented ingredient that allows specific changes, both in the composition and/or activity in the gastrointestinal microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 10 g/day, preferably 2 to 9 g/day, more preferably 3 to 8 g/day. In another embodiment, the prebiotic may be used according to the present invention in an amount of 5 to 50 g/day, preferably 10 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isdrnaltulose (Palatinose™), isomalto-oligosaccharides, gluco-oligosaccharides, xylo-oligosaccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

In some embodiments, a combination of *Bifidobacterium* (and any additional probiotic microorganisms, if present) bacteria and prebiotics according to the present invention exhibits a synergistic effect in certain applications (i.e. an effect which is greater than the additive effect of the bacteria when used separately). Without wishing to be bound by theory, it is believed that such a combination is capable of selectively stimulating the growth and/or activity of the *Bifidobacteria* (and any additional probiotic microorganisms, if present) bacteria in the colon, and thus improve host health.

Suitably, the prebiotic used in the combination is polydextrose.

Example 1

Materials and Methods

C57Bl/6J mice were obtained from Jackson Laboratories. A 10-day protocol was conducted to see whether the positive effect of B420 on infarct size can be seen before the probiotic colonizes the gut. At 10 weeks of age, mice were first fed a high-fat diet (58% of calories from fat) for two weeks before initiating a 10-day treatment, once per day, with vehicle or *Bifidobacterium animalis* ssp. *lactis* 420 B420 ($10^9$ CFU/day).

Cardiac Ischemia-Reperfusion Protocol

Following each gavage sequence, mice were subjected to the cardiac ischemia-reperfusion protocol. Mice were anesthetized with an intraperitoneal injection of 250 mg/kg tribromoethanol, intubated and ventilated with 0.5-2.0% isoflurane. To maintain body temperature and restore potential loss of fluid, 500 µl of warmed sterile saline was injected into the dorsal subcutaneous space. The heart was exposed and the left coronary artery was visualized following a left anterior thoracotomy. The left coronary artery was occluded using 7-0 suture compressing a small piece of tubing (PE-10) to prevent vessel damage during occlusion. After 30 minutes of occlusion, the ligature was removed and the animal was allowed to recover.

During the occlusion of the left coronary artery, the heart suffers ischemia, which is then reperfused after 30 minutes. This reperfusion causes inflammation in the ischemic regions of the heart.

Histological Assessment of Infarct Size

Following 3 days of reperfusion, mice were sacrificed and hearts were immediately sectioned (1 mm) and double-stained with Evans blue and triphenyltetrazolium chloride (TTC) to define the necrotic area and the area subjected to ischemia (area at risk). After incubation, infarcted myocardium stained white (Area of Necrosis), viable tissue within Area at Risk stained red, and perfused tissue remained blue. Infarct size was determined as Area of Necrosis vs. Area at Risk. The area of infarction had been validated by staining sections for IL-6 and ICAM-1 the inflammatory markers correlated well with the infarcted area as determined with Evans blue staining.

Results

Figure 2:
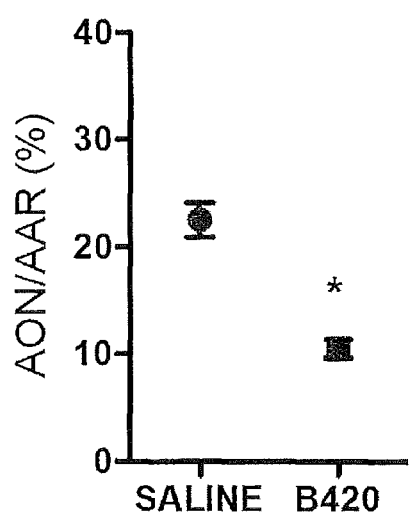
FIG. 2 is a graph comparing infarct size (AON/AAR) in HFD-fed mice treated with B420 according to the present invention (Example 1) and saline (control)

FIG. 1 illustrates the infarct size in high-fat diet-fed mice following a 10-day short term treatment with B420 shown as representative histology. FIG. 2 is a graph of infarct size with all data points included (N=18 for saline, N=13 for B420). Although B420 would have likely not colonized the gut within 10 days of treatment, the results show B420 reduced infarct size in mice by more than 50%. This demonstrates that the probiotic can be very effective even in short-term treatment.

Comparative Example 1

As a comparison, an on-off gavage protocol was conducted to see whether B420 ingestion needs to be continuous in order to reduce infarct size. Mice were first fed a high-fat diet for two weeks before the following sequence: 5 days gavage ($10^9$ CFU/day), 5 days off, and the sequence was repeated 3 times. Mice were then gavaged for a final 5 days with B420.

Figure 3:
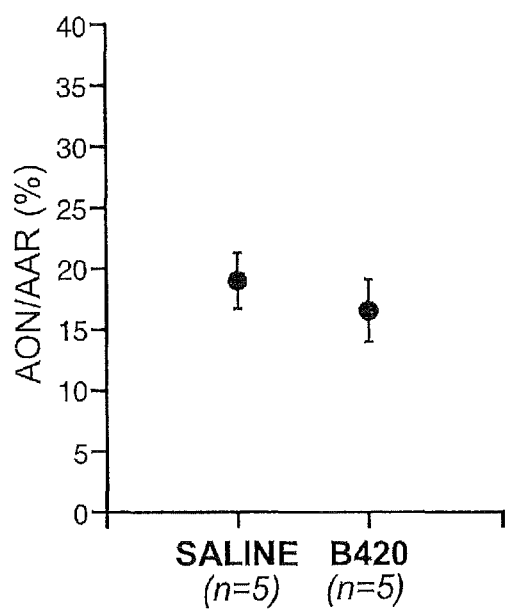
FIG. 3 illustrates the infarct size in mice gavaged in a 5-day on-off protocol with B420 according to Comparative Example 1.

The results are shown in FIG. 3 showing infarct size in mice gavaged on-off with B420. The results show that short 5-day gavages were insufficient to produce a similar reduction in infarct size in high-fat fed mice (FIG. 3).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in medicine, biology, biochemistry and biotechnology or related fields are intended to be within the scope of the following claims.

The invention claimed is:

1. A method for treating cardiovascular disease in a mammal in need thereof, wherein the method comprises administering an effective amount of a bacterium of the genus *Bifidobacterium* to the mammal for a period of at least 7 days and not exceeding 18 days, wherein the mammal is experiencing or displaying a pathology or symptomatology of the cardiovascular disease.

2. The method of claim 1, wherein the cardiovascular disease is selected from aneurysm, angina, atherosclerosis, cerebrovascular accident (stroke), cerebrovascular disease, congestive heart failure (CHF), dilated cardiomyopathy, inflammatory heart disease, coronary artery disease, myocardial infarction (heart attack) and peripheral vascular disease.

3. The method of claim 2, wherein the cardiovascular disease is myocardial infarction.

4. The method of claim 2, wherein the cardiovascular disease is congestive heart failure.

5. The method of claim 2, wherein the cardiovascular disease is dilated cardiomyopathy.

6. The method of claim 2, wherein the cardiovascular disease is inflammatory heart disease.

7. The method of claim 6, wherein the inflammatory heart disease is selected from endocarditis, inflammatory cardiomegaly and myocarditis.

8. The method of claim 1, wherein the bacterium is administered for a period of at least 9 days and not exceeding 14 days.

9. The method of claim 1, wherein the bacterium is administered once a day for the administration period.

10. The method of claim 1, wherein the mammal in need of the treatment ingests a high-fat diet over a two-week period immediately preceding the treatment.

11. The method of claim 1, wherein the *Bifidobacterium* is a probiotic *Bifidobacterium*.

12. The method of claim 1, wherein the bacterium is of the species selected from the group consisting of *Bifidobacterium bifidum, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*.

13. The method of claim 12, wherein the bacterium is of the species *Bifidobacterium animalis*.

14. The method of claim 13, wherein the bacterium is of the species *Bifidobacterium animalis* subsp. *lactis*.

15. The method of claim 14, wherein the bacterium is of the species *Bifidobacterium animalis* subsp. *lactis* strain 420 (B420).

16. The method of claim 1, wherein the *Bifidobacteria* is administered as a component of a food product.

17. The method of claim 16, wherein the *Bifidobacteria* is administered as a component of a yogurt.

18. The method of claim 1, wherein the *Bifidobacteria* is administered as a component of a dietary supplement.

19. The method of claim 1, wherein the *Bifidobacteria* is administered as a component of a pharmaceutical composition.

20. The method of claim 1, wherein the *Bifidobacteria* is administered at a dosage of from about $10^6$ to about $10^{12}$ CFU of bacteria/dose.

21. The method of claim 20, wherein the *Bifidobacteria* is administered at a dosage of about $10^9$ to about $10^{11}$ CFU of bacteria/dose.

22. The method of claim 17, wherein the yoghurt contains from about $10^8$ to $10^{12}$ CFU of the bacteria per dose.

23. The method of claim 11, wherein the method comprises administering a mixture of probiotic *Bifidobacteria*.

24. The method of claim 12, wherein the method comprises administering a mixture of bacterial species selected from the group consisting of *Bifidobacterium bifidum, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*.

25. The method of claim 1, wherein the period over which the bacterium is administered does not exceed 12 days.

26. The method of claim 1, wherein the period over which the bacterium is administered does not exceed 11 days.

27. The method of claim 1, wherein the bacterium is administered for a period of at least 10 days and not exceeding 12 days.

28. The method of claim 1, wherein the mammal is a human.

* * * * *